United States Patent

Yabuki et al.

(10) Patent No.: US 6,641,841 B2
(45) Date of Patent: Nov. 4, 2003

(54) TABLET COMPOSITION

(75) Inventors: Akira Yabuki, Kawasaki (JP); Masato Kaida, Kawasaki (JP); Takahiko Ando, Kawasaki (JP); Nobutaka Ninomiya, Kawasaki (JP); Masanao Ozaki, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/920,830

(22) Filed: Aug. 3, 2001

(65) Prior Publication Data

US 2002/0028239 A1 Mar. 7, 2002

Related U.S. Application Data

(62) Division of application No. 09/672,896, filed on Sep. 29, 2000, now Pat. No. 6,296,872, which is a continuation of application No. 09/311,060, filed on May 14, 1999, now Pat. No. 6,143,323, which is a continuation of application No. PCT/JP97/04152, filed on Nov. 14, 1997.

(30) Foreign Application Priority Data

Nov. 15, 1996 (JP) ............................................. 8-318541

(51) Int. Cl.[7] .............................. A61K 9/20; A61K 9/28; A61K 9/36
(52) U.S. Cl. ........................ 424/480; 424/464; 424/465; 424/474; 514/866
(58) Field of Search .................................. 424/464, 465, 424/489, 474, 475, 480, 482, 479; 514/866

(56) References Cited

U.S. PATENT DOCUMENTS 4,816,484 A * 3/1989 Toyoshima et al. .......... 514/563
6,143,323 A 11/2000 Yabuki et al. .............. 424/464
6,296,872 B1 * 10/2001 Yabuki et al. .............. 424/464

OTHER PUBLICATIONS

Pharmaceutical Macromolecular Material Science, pp 77–79, Chinese Medicament Science & Technology Press, Apr. 30, 1993.*

Y. Kawashima, et al., "Preparation of a Sustained–Release Matrix Tablet of Acetaminophen with Pulverized Low–Substituted Hydroxypropylcellulose Via Dry Granulation", Chemical & Pharmaceutical Bulletin, vol. 41, No. 10, pp. 1827–1831 (Oct., 1993).

Statement of Clinical Testing Mar. 1995.

* cited by examiner

*Primary Examiner*—James M. Spear
(74) *Attorney, Agent, or Firm*—Oblon, Spivak, McClelland, Maier & Neustadt, P.C.

(57) ABSTRACT

A tablet composition containing N-(trans-4-isopropylcyclohexanecarbonyl)-D-phenylalanine and low substituted hydroxypropylcellulose is disclosed. This tablet composition is rapidly disintegrated in the stomach after the administration and absorbed without being influenced by meals to inhibit the rise of the blood sugar levels of diabetics after meals.

6 Claims, 1 Drawing Sheet

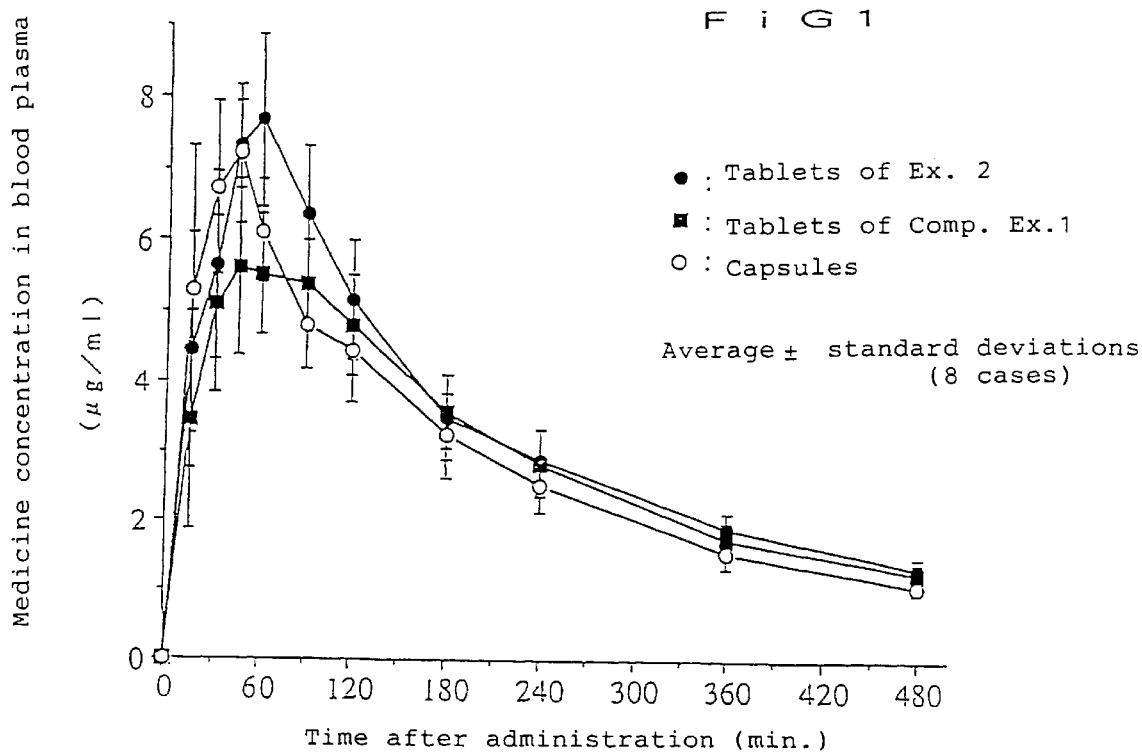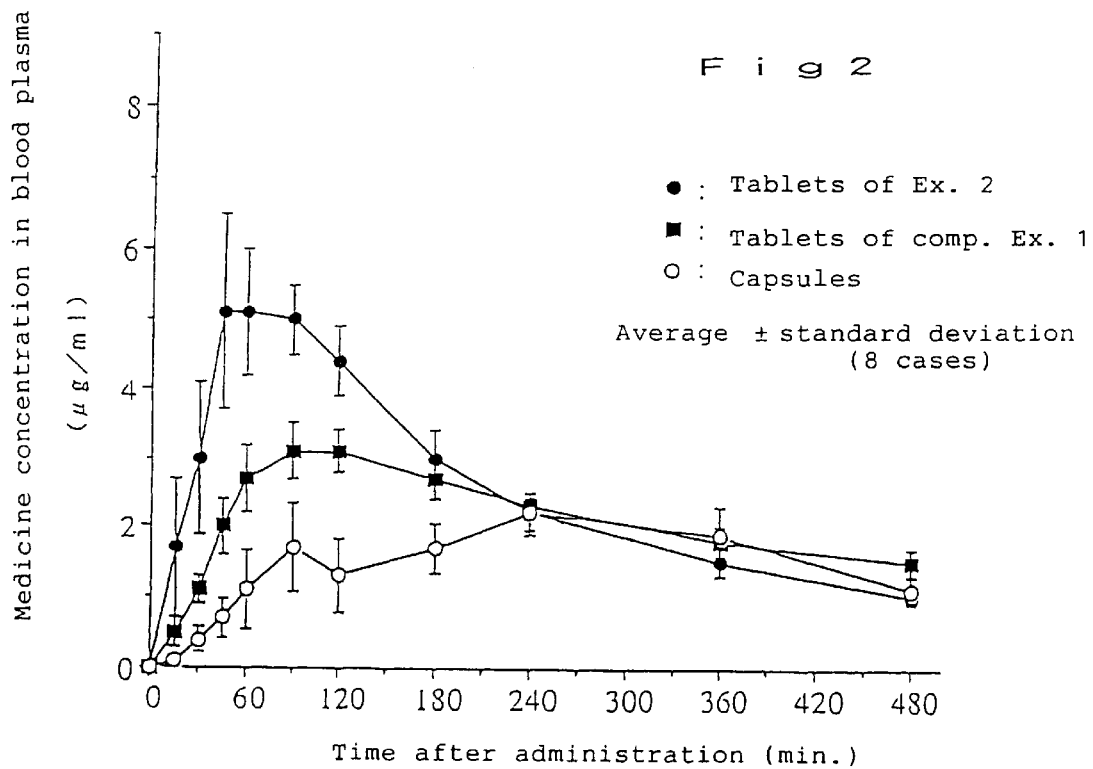

TABLET COMPOSITION

This application is a Division of application Ser. No. 09/672,896 filed on Sep. 29, 2000, now U.S. Pat. No. 6,296,872, which is a continuation of application Ser. No. 09/311,060, filed May 14, 1999, now U.S. Pat. No 6,143,323, issued Nov. 7, 2000, which is a continuation of International Application No. PCT/JP97/04152, filed Nov. 14, 1997.

TECHNICAL FIELD

The present invention relates to a tablet composition used for controlling the blood sugar levels of diabetics.

BACKGROUND OF THE INVENTION

It is known that N-(trans-4-isopropylcyclohexanecarbonyl)-D-phenylalanine of the following formula:

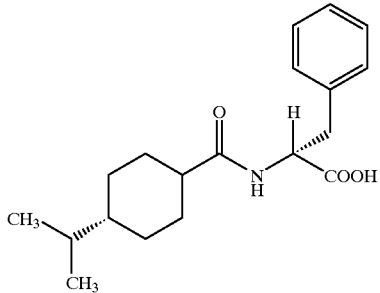

(hereinafter referred to as "compound [1]") exhibits an excellent effect of lowering the blood sugar level when it is taken orally, and is thus usable as a medicine for diabetes [Japanese Patent Publication for Opposition Purpose (hereinafter referred to as "J. P. KOKOKU") No. Hei 4-15221].

However, it was found that when compound [1] is orally taken before or after a meal for the purpose of preventing the blood sugar level after the meal from rising, the bioavailability of the compound is lowered.

DISCLOSURE OF THE INVENTION

The object of the present invention is to provide a tablet composition which is rapidly absorbed without being influenced by the meals and without impairing the essential properties of compound [1] contained therein, which has an effect of lowering the blood sugar level and only a short effect-lasting time.

The present invention relates to a tablet composition containing compound [1] as the active ingredient and a low substituted hydroxypropylcellulose as a disintegrator.

The present invention also relates to a tablet composition containing a filler, preferably a filler containing lactose, in addition to said compound [1] and the low substituted hydroxypropylcellulose.

The present invention further relates to the above-described tablet composition which further contains a hydroxypropyl cellulose as a binder.

After the administration, the above-described tablet compositions are rapidly disintegrated in the stomach after the administration and absorbed without being influenced by the meals to prevent the blood sugar level of diabetics after meals from rising.

BRIEF DESCRIPTION OF DRAWINGS

FIG. 1 shows the concentration of compound [1] in the blood plasma of patients fasting from foods.

FIG. 2 shows the concentration of compound [1] in the blood plasma of patients, which was administered before meals.

BEST MODE FOR CARRYING OUT THE INVENTION

The active compound in the tablet composition of the present invention is N-(trans-4-isopropylcyclohexanecarbonyl)-D-phenylalanine [compound 1] of the above formula. Processes for producing compound [1] are described in J. P. KOKOKU No. Hei 4-15221 or the like. This compound can be obtained by, for example condensing 4-isopropylcyclohexanecarboxylic acid with D-phenylalanine or an ester thereof by, for example, active ester method. Processes for obtaining stable crystals of this compound are described in Japanese Patent Unexamined Published Application (hereinafter referred to as "J. P. KOKAI") No. Hei 5-208943. For example, compound [1] can be obtained by crystallizing from a mixed solvent of ethanol, acetone or the like and water at a temperature of not lower than 10° C.

The amount of compound [1] in the tablet composition of the present invention is usually 5 to 50% by weight, preferably 10 to 40% by weight, and more preferably 20 to 30% by weight.

The low substituted hydroxypropylcellulose contained as a disintegrator in the tablet composition of the present invention is a hydroxypropyl ether of cellulose obtained by etherifying only a part of hydroxyl groups of pyranose ring of a cellulose with propylene oxide. When dried low substituted hydroxypropylcellulose is determined, the hydroxypropyl group content thereof is 5.0 to 16.0% by weight (refer to the Japanese Pharmacopeia, $13^{th}$ Revision, D-885 to D-888 and U.S. Pharmacopeia, $23^{rd}$ Revision, pages 2253 to 2254). Examples of the low substituted hydroxypropylcellulose include low substituted hydroxypropylcellulose L-HPC (LH-11, LH-20, LH-21, LH-22, LH-30, LH-31 and LH-32; products of Shin-Etsu Chemical Co., Ltd.).

The amount of the low substituted hydroxypropylcellulose is usually 5 to 50% by weight, preferably 5 to 40% by weight, more preferably 10 to 40% by weight, and most preferably 20 to 40% by weight.

Sodium carboxymethyl cellulose, calcium carboxymethyl cellulose, croscarmellose sodium, etc. are not preferred because they are colored during the storage. Although corn starch, sodium carboxymethyl starch, crystalline cellulose, partly pregelatinized starch, etc. having a low disintegrating property is not preferably used alone, but the disintegrating property thereof is improved by combining each of them with low sustituted hydroxypropylcellulose.

The tablet composition of the present invention can further contain lactose, starch, crystalline cellulose, calcium monohydrogen phosphate, light anhydrous silicic acid, titanium oxide, magnesium aluminometasilicate as the filler, in addition to the above-described indispensable ingredients. Among them, lactose is preferred because it is not easily incompatible with compound [1]. The amount of the filler can be the balance in the tablet composition. It is preferably 10 to 90% by weight, more preferably 20 to 80% by weight and more preferably 30 to 60% by weight.

Further, it is desirable to incorporate 0.1 to 5% by weight, preferably 0.5 to 2% by weight, of hydroxypropylcellulose as a binder so as to facilitate the granulation in the manufacturing process. Hydroxypropylcellulose used for this purpose is different from the above-described low substituted hydroxypropylcellulose. The quantity of hydroxypropoxyl group in dry hydroxypropylcellulose is determined to be 53.4 to 77.5% by weight (refer to the Japanese Pharmacopeia, 13$^{th}$ Revision, D-880 to D-885 and U.S. Pharmacopeia, 23$^{rd}$ Revision, page 2253). Such hydroxypropylcellulose is easily available as HPC-L, L(fine powder) or the like (products of Nippon Soda Co., Ltd.).

The tablet composition of the present invention can contain additives usually incorporated into tablet compositions in addition to the above-described ingredients so far as the effect of the present invention is not impaired. The additives include fillers such as crystalline cellulose, calcium monohydrogen phosphate, starch, light anhydrous silicic acid, titanium oxide, magnesium aluminometasilicate and polyethylene glycol; disintegrators such as starch, crystalline cellulose, hydroxypropyl starch and partly pregelatinized starch; binders such as gelatin, acacia, ethyl cellulose and polyvinyl alcohol; lubricants such as stearic acid, magnesium stearate, calcium stearate, talk and hydrogenated oil; coating agents such as hydroxypropylmethyl cellulose, hydroxypropyl cellulose, methyl cellulose, ethyl cellulose, hydroxypropylmethyl cellulose phthalate, polyvinylacetal diethylaminoacetate, aminoalkyl methacrylate copolymers and polyvinyl acetate phthalate; colorants such as tar colorant and titanium oxide; corrigents such as citric acid, adipic acid, ascorbic acid and menthol; and surfactants such as glycerol monostearate, polysorbates, sodium laurylsulfate and sucross esters of fatty acids.

The tablet composition of the present invention can be prepared by an ordinary wet granulation method, wherein the above-described ingredients are thoroughly mixed and then granulated with water which may contain a lower alcohol such as ethanol or isopropanol, the granules thus obtained are dried and, if necessary, reduced in size and tableted with a tableting machine. The tablets thus obtained can be coated, if desired.

The following Examples will further illustrate the present invention.

EXAMPLE 1

The ingredients shown in Table 1 were weighed, and all the ingredients excluding magnesium stearate were mixed with a highshear mixer for 10 minutes. Purified water in such an amount (15 to 75 parts by weight) that granules having a diameter of 100 to 500 $\mu$m would be obtained was added thereto, and the resultant mixture was granulated with a highshear mixer for 10 minutes. The thus-obtained granules were reduced in size with a mill and then dried. Magnesium stearate was added to the dry granules thus obtained, and the thus-obtained mixture was blended with a V-shaped blender for 2 minutes and tableted to obtain tablets having a diameter of 7 mm, thickness of 3 mm and weight of 100 mg. The disintegration time of the thus-obtained tablets in water was determined according to a disintegration test of the Japanese Pharmacopeia. L-HPC(LH-31) (a product of Shin-Etsu Chemical Co., Ltd.) having a hydroxypropoxyl group content of 10 to 12.9% by weight and an average particle diameter of not larger than 30 $\mu$m was used as the low substituted hydroxypropylcellulose. The results are shown in Table 1.

TABLE 1

| | Comparative composition | | | | | Composition of the present invention | | | | |
|---|---|---|---|---|---|---|---|---|---|---|
| | 1 | 2 | 3 | 4 | 5 | 6 | 7 | 8 | 9 | 10 |
| Compound [1] | 25 | 25 | 25 | 25 | 25 | 25 | 25 | 25 | 25 | 25 |
| Lactose | 74 | 49 | 44 | 54 | 64 | 54 | 44 | 44 | 34 | 44 |
| Corn starch | | 20 | 10 | | | | 20 | | 10 | |
| Na carboxymethyl starch | | | | | 10 | | | | | 10 |
| Partly pregelatinized starch | | | | 10 | | | | | 10 | |
| Crystalline cellulose | | 5 | 20 | 10 | | | | 10 | 10 | |
| Low substituted hydroxypropylcellulose | | | | | | 20 | 10 | 20 | 10 | 20 |
| Magnesium stearate | 1 | 1 | 1 | 1 | 1 | 1 | 1 | 1 | 1 | 1 |
| Disintegration time(min) | >30 | >30 | >30 | >30 | 11 | 0.8 | 3.1 | 3.1 | 3.0 | 3.8 |

It is apparent from Table 1 that tablets prepared by using a low substituted hydroxypropylcellulose as the disintegrator were disintegrated more rapidly than tablets prepared by using another disintegrator.

EXAMPLE 2

250 g of compound [1], 530 g of lactose and 200 g of low substituted hydroxypropylcellulose (LH-31; a product of Shin-Etsu Chemical Co., Ltd.) having a hydroxypropoxyl group content of 10.0 to 13.0% by weight and an average particle diameter of not larger than 30 $\mu$m were thoroughly mixed with a highshear mixer. 10 g of hydroxypropyl cellulose (HPC-L; a product of Nippon Soda Co., Ltd.) dissolved in 500 g of purified water was added thereto and the obtained mixture was granulated with a highshear mixer. The granules thus obtained were reduced in size and dried. 10 g of magnesium stearate was added to the powder and the thus-obtained mixture was tableted to obtain tablets having a diameter of 7 mm, thickness of 3.7 mm and weight of 120 mg and containing 30 mg of compound [1]. The tablets were spray-coated with a coating liquid comprising 8 g of hydroxypropylmethyl cellulose, 1.5 g of polyethylene glycol 6000, 2.4 g of talc, 0.5 of titanium oxide and 87.6 g of purified water to obtain the coated tablets.

COMPARATIVE EXAMPLE 1

250 g of compound [1], 440 g of lactose, 100 g of corn starch and 200 g of crystalline cellulose were thoroughly mixed with a highshear mixer. 3.0 g of hydroxypropyl cellulose (HPC-L; a product of Nippon Soda Co., Ltd.) dissolved in 360 g of purified water was added thereto and the obtained mixture was granulated with a highshear mixer. The granules thus obtained were reduced in size and dried. 10 g of magnesium stearate was added to the powder and the obtained mixture was tableted to obtain tablets having a diameter of 7 mm, thickness of 3.7 mm and weight of 120 mg and containing 30 mg of compound [1]. The tablets were spray-coated with a coating liquid comprising 8 g of hydroxypropylmethyl cellulose, 1.5 g of polyethylene glycol 6000, 2.4 g of talc, 0.5 g of titanium oxide and 87.6 g of purified water to obtain the coated tablets.

The influences of foods on the oral absorption of the tablets obtained in Example 2 and Comparative Example 1 were examined. As the controls, No. 3 hard gelatin capsules each containing 30 mg of compound [1] and 70 mg of lactose were used. The tablets or capsules were orally administered to beagles (n=8), and foods were given five minutes after. Blood samples were taken 0, 15, 30, 45, 60, 90, 120, 180, 240, 360 and 480 minutes after the administration and the concentration of compound [1] in the blood plasma was determined by HPLC. The time for attaining the maximum blood concentration (Tmax), the maximum blood concentration (Cmax) and the area under the curve of the blood concentration (AUC) were determined. For comparison, the same tests were repeated except that the tablets or capsules were administered to the fasting beagles. The results are shown in Table 2 and FIGS. 1 and 2.

TABLE 2

| | | Cmax ($\mu$g/ml) | Tmax (min) | AUC ($\mu$g.min/ml) |
|---|---|---|---|---|
| Tablets of Ex. 2 | Before meal | 6.6 ± 3.3 | 68 ± 30 | 1218 ± 278 |
| | Fasting | 9.7 ± 2.6 | 47 ± 36 | 1635 ± 526 |
| Tablets of Comp. Ex. 1 | Before meal | 3.5 ± 0.9 | 131 ± 96 | 1018 ± 200 |
| | Fasting | 7.5 ± 3.3 | 64 ± 41 | 1462 ± 542 |
| Capsules | Before meal | 3.1 ± 1.1 | 226 ± 145 | 738 ± 210 |
| | Fasting | 9.5 ± 2.3 | 38 ± 36 | 1445 ± 453 |

(Average ± standard deviation, n = 8)

It is apparent from Table 2 and FIG. 1 that when the tablet composition of the present invention was administered to the fasting beagles, the absorption thereof was equivalent to, or slightly superior to that of the tablet composition and capsules of Comparative Example 1. On the contrary, when the tablet composition of the present invention was administered before meals on the assumption that it is practically used in that way, it was rapidly absorbed without being influenced by foods and it could inhibit the rise of the blood sugar level of diabetics after meals, while when the tablet composition or capsules of Comparative Example 1 were used in Comparative Example 1, the absorption of compound [1] was low and impractical.

EXAMPLE 3

330 g of compound [1], 450 g of lactose and 200 g of a low sustituted hydroxypropylcellulose (LH-31; a product of Shin-Etsu Chemical Co., Ltd.) were thoroughly mixed with a highshear mixer. 10 g of hydroxypropyl cellulose (HPC-L; a product of Nippon Soda Co., Ltd.) dissolved in 500 g of purified water was added thereto and the obtained mixture was granulated with a highshear mixer. The granules thus obtained were reduced in size and dried. 10 g of magnesium stearate was added to the powder and the obtained mixture was tableted to obtain tablets having a diameter of 7 mm, thickness of 3.7 mm and weight of 121 mg and containing 40 mg of compound [1]. The tablets were spray-coated with a coating liquid comprising 8 g of hydroxypropylmethyl cellulose, 1.5 g of polyethylene glycol 6000, 2.4 g of talc, 0.5 g of titanium oxide and 87.6 g of purified water to obtain the coated tablets.

The influences of foods on the oral absorption of the coated tablets obtained as described above were examined. The coated tablets had an absorption superior to that of the tablets or capsules of Comparative Example 1, like the coated tablets of Example 2, when they were administered during the fasting or before meals. In particular, the coated tablets could inhibit the rise of the blood sugar level of diabetics after meals,

EXAMPLE 4

125 g of compound [1], 655 g of lactose and 200 g of low substituted hydroxypropylcellulose (LH-31; a product of Shin-Etsu Chemical Co., Ltd.) were thoroughly mixed with a highshear mixer. 10 g of hydroxypropyl cellulose (HPC-L; a product of Nippon Soda Co., Ltd.) dissolved in 500 g of purified water was added thereto and the obtained mixture was granulated with a highshear mixer The granules thus obtained were reduced in size and dried. 10 g of magnesium stearate was added to the powder and the obtained mixture was tableted to obtain tablets having a diameter of 7 mm, thickness of 3.7 mm and weight of 120 mg and containing 15 mg of compound [1]. The tablets were spray-coated with a coating liquid comprising 8 g of hydroxypropylmethyl cellulose, 1.5 g of polyethylene glycol 6000, 2.4 g of talc, 0.5 g of titanium oxide and 87.6 g of purified water to obtain the coated tablets.

The influences of foods on the oral absorption of the coated tablets obtained as described above were examined. The coated tablets had an absorption superior to that of the tablets or capsules of Comparative Example 1, like the coated tablets of Example 2, when they were administered during the fasting or before meals. In particular, the coated tablets could inhibit the rise of the blood sugar level of diabetics after meals,

EXAMPLE 5

250 g of compound [1], 430 g of lactose, 100 g of crystalline cellulose and 200 g of low substituted hydroxypropylcellulose (LH-31; a product of Shin-Etsu Chemical Co., Ltd.) were thoroughly mixed with a highshear mixer. 10 g of hydroxypropyl cellulose (HPC-L; a product of Nippon Soda Co., Ltd.) dissolved in 570 g of purified water was added thereto and the obtained mixture was granulated with a highshear mixer. The granules thus obtained were reduced in size and dried. 10 g of magnesium stearate was added to the powder and the obtained mixture was tableted to obtain tablets having a diameter of 7 mm, thickness of 3.7 mm and weight of 120 mg and containing 30 mg of compound [1]. The tablets were spray-coated with a coating liquid comprising 8 g of hydroxypropylmethyl cellulose, 1.5 g of polyethylene glycol 6000, 2.4 g of talc, 0.5 g of titanium oxide and 87.6 g of purified water to obtain the coated tablets.

The influences of foods on the oral absorption of the coated tablets obtained as described above were examined.

The coated tablets had an absorption superior to that of the tablets or capsules of Comparative Example 1, like the coated tablets of Example 2, when they were administered during the fasting or before meals. In particular, the coated tablets could inhibit the rise of the blood sugar level of diabetics after meals,

EXAMPLE 6

250 g of compound [1], 320 g of lactose, 100 g of corn starch, 100 g of crystalline cellulose, 100 g of partly pregelatinized starch and 100 g of hydroxypropyl cellulose (LH-31; a product of Shin-Etsu Chemical Co., Ltd.) were thoroughly mixed with a highshear mixer. 10 g of hydroxypropyl cellulose (HPC-L; a product of Nippon Soda Co., Ltd.) dissolved in 450 g of purified water was added thereto and the obtained mixture was granulated with a highshear mixer. The granules thus obtained were reduced in size and dried. 10 g of magnesium stearate was added to the powder and the obtained mixture was tableted to obtain tablets having a diameter of 7 mm, thickness of 3.7 mm and weight of 100 mg and containing 30 mg of compound [1]. The tablets were spray-coated with a coating liquid comprising 8 g of hydroxypropylmethyl cellulose, 1.5 g of polyethylene glycol 6000, 2.4 g of talc, 0.5 g of titanium oxide and 87.6 g of purified water to obtain the coated tablets.

The influences of foods on the oral absorption of the coated tablets obtained as described above were examined. The coated tablets had an absorption superior to that of the tablets or capsules of Comparative Example 1, like the coated tablets of Example 2, when they were administered during the fasting or before meals. In particular, the coated tablets could inhibit the rise of the blood sugar level of diabetics after meals,

EXAMPLE 7

250 g of compound [1], 430 g of lactose, 100 g of sodium carboxymethyl starch and 200 g of low substituted hydroxypropylcellulose (LH-31; a product of Shin-Etsu Chemical Co., Ltd.) were thoroughly mixed with a highshear mixer. 10 g of hydroxypropyl cellulose (HPC-L; a product of Nippon Soda Co., Ltd.) dissolved in 640 g of purified water was added thereto and the obtained mixture was granulated with a highshear mixer. The granules thus obtained were reduced in size and dried. 10 g of magnesium stearate was added to the powder and the obtained mixture was tableted to obtain tablets having a diameter of 7 mm, thickness of 3.7 mm and weight of 120 mg and containing 30 mg of compound [1]. The tablets were spray-coated with a coating liquid comprising 8 g of hydroxypropylmethyl cellulose, 1.5 g of polyethylene glycol 6000, 2.4 g of talc, 0.5 g of titanium oxide and 87.6 g of purified water to obtain the coated tablets.

The influences of foods on the oral absorption of the coated tablets obtained as described above were examined. The coated tablets had an absorption superior to that of the tablets or capsules of Comparative Example 1, like the coated tablets of Example 2, when they were administered during the fasting or before meals. In particular, the coated tablets could inhibit the rise of the blood sugar level of diabetics after meals, As described above in detail, the tablet composition of N-(trans-4-isopropylcyclohexanecarbonyl)-D-phenylalanine which is rapidly absorbed to exhibit the effect of lowering the blood sugar level without being influenced by meals can be provided by the present invention.

What is claimed is:

1. A process for preparing a tablet comprising:

mixing N-(trans-4-isopropylcyclohexanecarbonyl)-D-phenylalanine and a disintegrant selected from the group consisting of low substituted hydroxypropylcellulose, sodium carboxymethyl cellulose, calcium carboxymethyl cellulose and croscaramellose sodium, to obtain a mixture, granulating said mixture with water which optionally contains a lower alcohol to obtain granules, drying said granules, and tableting said dried granules to obtain a tablet.

2. The process of claim 1, further comprising coating said tablet to obtain a coated tablet.

3. The process of claim 1, wherein said tablet is spray coated.

4. The process of claim 3, wherein the tablet is spray coated with a coating liquid comprising hydroxypropylmethyl cellulose.

5. A tablet produced by the process of claim 1.

6. A method for inhibiting the rise of blood sugar comprising administering the tablet of claim 5 to a subject in need thereof.

* * * * *

UNITED STATES PATENT AND TRADEMARK OFFICE
CERTIFICATE OF CORRECTION

PATENT NO.       : 6,641,841 B2
APPLICATION NO.  : 09/920830
DATED            : November 4, 2003
INVENTOR(S)      : Akira Yabuki et al.

It is certified that error appears in the above-identified patent and that said Letters Patent is hereby corrected as shown below:

Column 8, lines 28-29, "cellulose and croscaramellose sodium" should read --cellulose, croscarmellose sodium,--.

Signed and Sealed this

Sixth Day of February, 2007

JON W. DUDAS
*Director of the United States Patent and Trademark Office*